United States Patent
Kaye et al.

(10) Patent No.: US 11,401,235 B2
(45) Date of Patent: Aug. 2, 2022

(54) SYNTHESIS OF TERPHENYL COMPOUNDS

(71) Applicant: Vectus Biosystems Limited, Rosebery (AU)

(72) Inventors: Anthony Kaye, Gisborne South (AU); Nurul Quazi, Doncaster (AU); George Feast, Balaclava (AU); Marshnil Lakshman, Hallam (AU)

(73) Assignee: VECTUS BIOSYSTEMS LIMITED, North Ryde (AU)

( * ) Notice: Subject to any disclaimer, the term of this patent is extended or adjusted under 35 U.S.C. 154(b) by 0 days.

(21) Appl. No.: 16/918,439

(22) Filed: Jul. 1, 2020

(65) Prior Publication Data
US 2020/0399202 A1    Dec. 24, 2020

Related U.S. Application Data

(62) Division of application No. 15/761,862, filed as application No. PCT/AU2016/050864 on Sep. 21, 2016, now Pat. No. 10,752,578.

(30) Foreign Application Priority Data

Sep. 22, 2015 (AU) .................. 2015903864

(51) Int. Cl.
C07C 231/02 (2006.01)
C07C 309/66 (2006.01)
(Continued)

(52) U.S. Cl.
CPC ............ C07C 231/02 (2013.01); C07C 51/09 (2013.01); C07C 53/134 (2013.01); C07C 59/52 (2013.01);
(Continued)

(58) Field of Classification Search
None
See application file for complete search history.

(56) References Cited

U.S. PATENT DOCUMENTS

| 5,324,743 A | 6/1994 | Dillard et al. |
| 10,752,578 B2 | 8/2020 | Kaye et al. |

(Continued)

FOREIGN PATENT DOCUMENTS

| EP | 2062900 A1 | 5/2009 |
| EP | 2272817 A1 | 1/2011 |
| WO | 2015/039173 A1 | 3/2015 |

OTHER PUBLICATIONS

STN Registry No. 1228970-34-0, 1 page, Jul. 2, 2010.
(Continued)

*Primary Examiner* — Sudhakar Katakam
*Assistant Examiner* — Jennifer C Sawyer
(74) *Attorney, Agent, or Firm* — McCarter & English, LLP; Matthew R. Van Eman

(57) ABSTRACT

The present invention relates novel methods of synthesizing terphenyl compounds and in particular to novel methods for the synthesis of a compound of Formula I

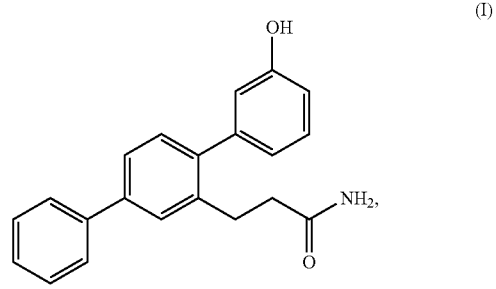

or intermediates thereof.

2 Claims, 14 Drawing Sheets

(51) Int. Cl.
    *C07C 69/732* (2006.01)
    *C07C 59/52* (2006.01)
    *C07C 303/28* (2006.01)
    *C07C 231/12* (2006.01)
    *C07C 235/34* (2006.01)
    *C07C 51/09* (2006.01)
    *C07C 53/134* (2006.01)
    *C07C 67/03* (2006.01)
    *C07C 67/31* (2006.01)
    *C07C 69/616* (2006.01)

(52) U.S. Cl.
    CPC .............. *C07C 67/03* (2013.01); *C07C 67/31* (2013.01); *C07C 69/616* (2013.01); *C07C 69/732* (2013.01); *C07C 231/12* (2013.01); *C07C 235/34* (2013.01); *C07C 303/28* (2013.01); *C07C 309/66* (2013.01)

(56) References Cited

U.S. PATENT DOCUMENTS

| | | |
|---|---|---|
| 2008/0275116 A1 | 11/2008 | Yamaguchi et al. |
| 2009/0153040 A1 | 6/2009 | Kim et al. |
| 2009/0312315 A1 | 12/2009 | Yamaguchi et al. |
| 2016/0221933 A1 | 8/2016 | Duggan |
| 2018/0072682 A1* | 3/2018 | Duggan .................. A61P 1/12 |

OTHER PUBLICATIONS

STN Registry No. 157230-51-8, 1 page, Aug. 24, 1994.
STN Registry No. 1678538-69-6, 1 page, Apr. 7, 2015.
Supplementary European Search Report for Application No. 16847641.4, dated Apr. 29, 2019, 15 pages.
U.S. Appl. No. 15/761,862, filed Mar. 21, 2018, U.S. Pat. No. 10,752,578, Issued.

\* cited by examiner

| Peak No. | Result | Ret. Time (min) | Time offset (min) | Area (counts) | Width 1/2 (sec) |
|---|---|---|---|---|---|
| 1 | 1.2182 | 4.289 | 0.000 | 3379 | 2.7 |
| 2 | 0.1562 | 6.750 | 0.000 | 433 | 1.4 |
| 3 | 0.0090 | 7.201 | 0.000 | 250 | 0.8 |
| 4 | 0.4172 | 8.032 | 0.000 | 1157 | 1.8 |
| 5 | 0.0361 | 8.869 | 0.000 | 100 | 0.7 |
| 6 | 0.5715 | 8.958 | 0.000 | 1585 | 0.0 |
| 7 | 0.0606 | 9.144 | 0.000 | 168 | 0.6 |
| 8 | 6.1957 | 9.208 | 0.000 | 171886 | 0.6 |
| 9 | 0.0915 | 10.910 | 0.000 | 254 | 1.4 |
| 10 | 91.1628 | 11.945 | 0.000 | 252875 | 2.9 |
| Totals | 99.9998 | | 0.000 | 277387 | |

SYNTHESIS OF TERPHENYL COMPOUNDS

CROSS REFERENCE TO RELATED APPLICATIONS

The present application is a divisional application of U.S. application Ser. No. 15/761,862, filed on Mar. 21, 2018, which is a 35 U.S.C. § 371 national stage filing of International Application No. PCT/AU2016/050875, filed on Sep. 21, 2016, which claims priority from Australian provisional patent application no. 2015903864, filed on Sep. 22, 2015. The entire contents of these applications are incorporated herein by reference in their entirety.

FIELD OF THE INVENTION

The present invention relates methods of synthesizing terphenyl compounds, in particular a compound of Formula I

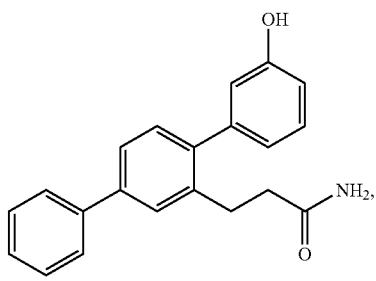

or intermediates thereof.

The invention has been developed primarily for use in the synthesis of the compound of Formula I and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

The compound of Formula I, known as VB0004, has been shown to have blood pressure lowering and/or anti-fibrotic effects in intravenous and oral dosing studies as disclosed in WO2015/039173 (PCT/AU2014/000923). VB0004 may also be represented by the following name: 2'-[3-hydroxy-(1,1':4',1''-terphenyl)]propanamide. VB0004 is effective in the prophylactic and/or therapeutic treatment of fibrosis by preventing fibrosis, slowing the progression of established fibrosis and/or reducing the degree (reversal) of established fibrosis. VB0004 may also be effective in the therapeutic treatment of hypertension and prehypertension, which are major factors in the development of heart, kidney and blood vessel damage, resulting in the replacement of normal functional tissue by scar tissue or fibrosis. The synthesis of VB0004 has been disclosed in WO2015/039173 (PCT/AU2014/000923). The present invention relates to new methods of synthesizing VB0004 that are suitable for large-scale production.

It is an object of the present invention to overcome or ameliorate at least one of the disadvantages of the prior art, or to provide a useful alternative.

SUMMARY OF THE INVENTION

According to one aspect, the present invention provides a method of producing a compound of Formula (I)

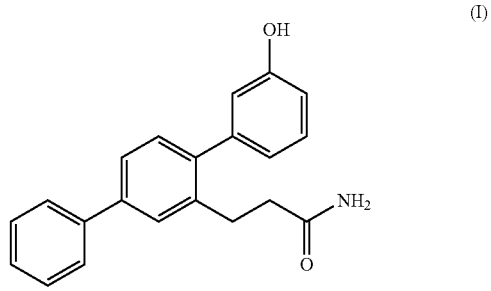 [SMILES: NC(=O)CCc1cc(-c2ccccc2)ccc1-c1cccc(O)c1]

or a pharmaceutically acceptable salt thereof, wherein the compound of Formula (I) is derived from any one or more of the compounds selected from the group consisting of:

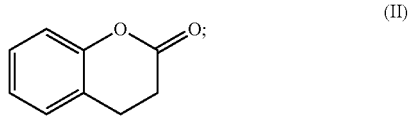

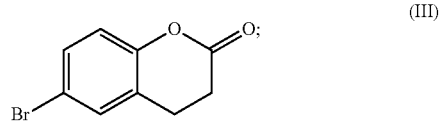

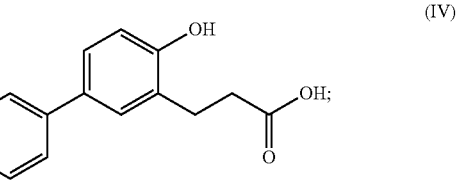

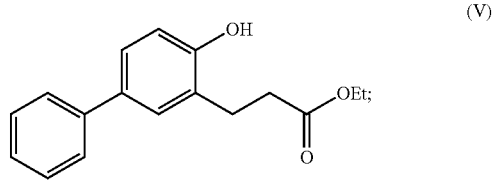 [SMILES: CCOC(=O)CCc1cc(-c2ccccc2)ccc1O]

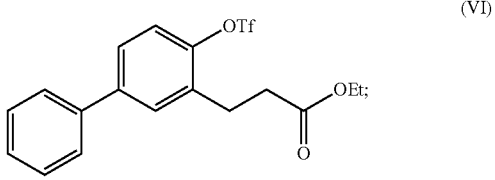 [SMILES: CCOC(=O)CCc1cc(-c2ccccc2)ccc1OS(=O)(=O)C(F)(F)F]

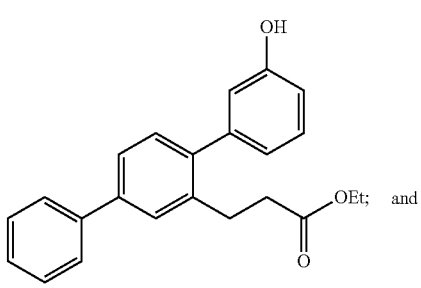

(VII)

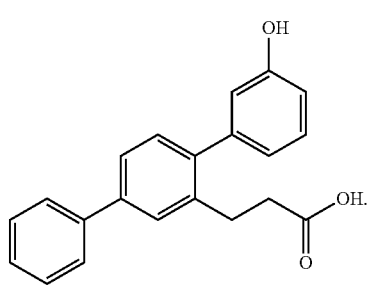

(VIII)

In one embodiment, the compound of Formula (I) is derived from the compound of Formula (II).

In another embodiment, the compound of Formula (I) is derived from the compound of Formula (III).

In another embodiment, the compound of Formula (I) is derived from the compound of Formula (IV).

In another embodiment, the compound of Formula (I) is derived from the compound of Formula (V).

In another embodiment, the compound of Formula (I) is derived from the compound of Formula (VI).

In another embodiment, the compound of Formula (I) is derived from the compound of Formula (VII).

In another embodiment, the compound of Formula (I) is derived from the compound of Formula (VIII).

In another embodiment, the method comprises the step of forming the compound of Formula (III) from the compound of Formula (II).

In another embodiment, the method comprises the step of forming the compound of Formula (IV) from the compound of Formula (III).

In another embodiment, the method comprises the step of forming the compound of Formula (V) from the compound of Formula (IV).

In another embodiment, the method comprises the step of forming the compound of Formula (VI) from the compound of Formula (V).

In another embodiment, the method comprises the step of forming the compound of Formula (VII) from the compound of Formula (VI).

In another embodiment, the method comprises the step of forming the compound of Formula (VIII) from the compound of Formula (VII).

In another embodiment, the method comprises the step of forming the compound of Formula (I) from the compound of Formula (VIII).

In another embodiment, the method comprises the following steps:
i) forming the compound of Formula (III) from the compound of Formula (II);
ii) forming the compound of Formula (IV) from the compound of Formula (III);
iii) forming the compound of Formula (V) from the compound of Formula (IV);
iv) forming the compound of Formula (VI) from the compound of Formula (V);
v) forming the compound of Formula (VII) from the compound of Formula (VI);
vi) forming the compound of Formula (VIII) from the compound of Formula (VII); and
vii) forming the compound of Formula (I) from the compound of Formula (VIII).

In another embodiment, the compound of Formula (III) is formed from the compound of Formula (II) by bromination.

In another embodiment, the compound of Formula (IV) is formed from the compound of Formula (III) by a Suzuki reaction.

In another embodiment, the compound of Formula (V) is formed from the compound of Formula (IV) by a Fischer esterification of a carboxylic acid.

In another embodiment, the compound of Formula (VI) is formed from the compound of Formula (V) by transformation of the phenol of the compound of Formula (V) into the corresponding triflate.

In another embodiment, the compound of Formula (VII) is formed from the compound of Formula (VI) by a Suzuki coupling reaction.

In another embodiment, the compound of Formula (VIII) is formed from the compound of Formula (VII) by a basic hydrolysis reaction.

In another embodiment, the compound of Formula (I) is formed from the compound of Formula (VIII) by bubbling ammonia gas through a solution of the compound of Formula (VIII), followed by isolation of the compound of Formula (I) by precipitation.

According to another aspect, the present invention relates to a compound of Formula (I)

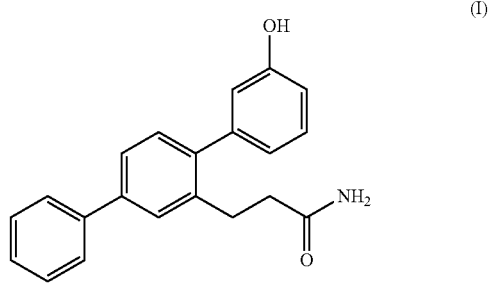 [SMILES: NC(=O)CCc1cc(-c2ccccc2)ccc1-c1cccc(O)c1]

(I)

or a pharmaceutically acceptable salt thereof, when produced by the method according to the invention.

In one embodiment, the compound has a purity of greater than 99%.

According to another aspect, the present invention relates to a compound of Formula (IV)

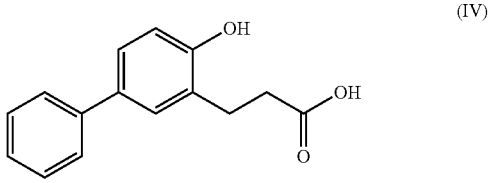

(IV)

or a pharmaceutically acceptable salt thereof.

According to another aspect, the present invention relates to a compound of Formula (V)

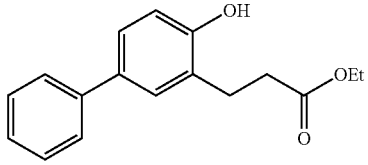
(V)

or a pharmaceutically acceptable salt thereof.

According to another aspect, the present invention relates to a compound of Formula (VI)

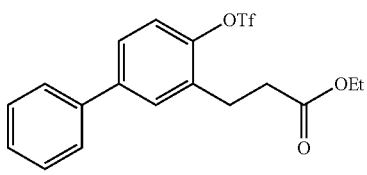
(VI)

or a pharmaceutically acceptable salt thereof.

According to another aspect, the present invention relates to a compound of Formula (VII)

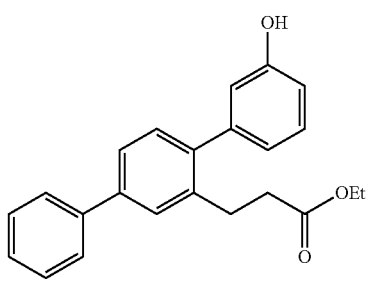
(VII)

or a pharmaceutically acceptable salt thereof.

According to another aspect, the present invention relates to a compound of Formula (VIII)

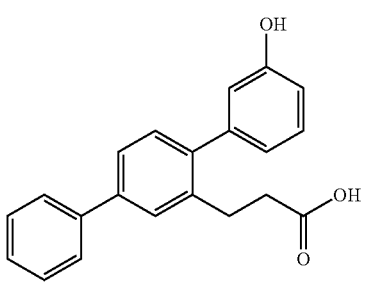
(VIII)

or a pharmaceutically acceptable salt thereof.

According to another aspect, the present invention relates to use of a compound of Formula (IV), (V), (VI), (VII) or (VIII) in the production of a compound of Formula (I)

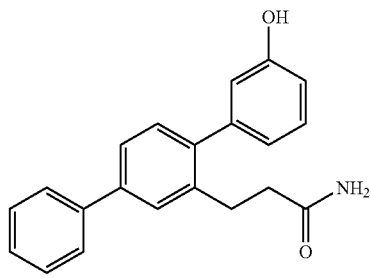
(I)

or a pharmaceutically acceptable salt thereof.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

DETAILED DESCRIPTION OF THE INVENTION

Figure 1:
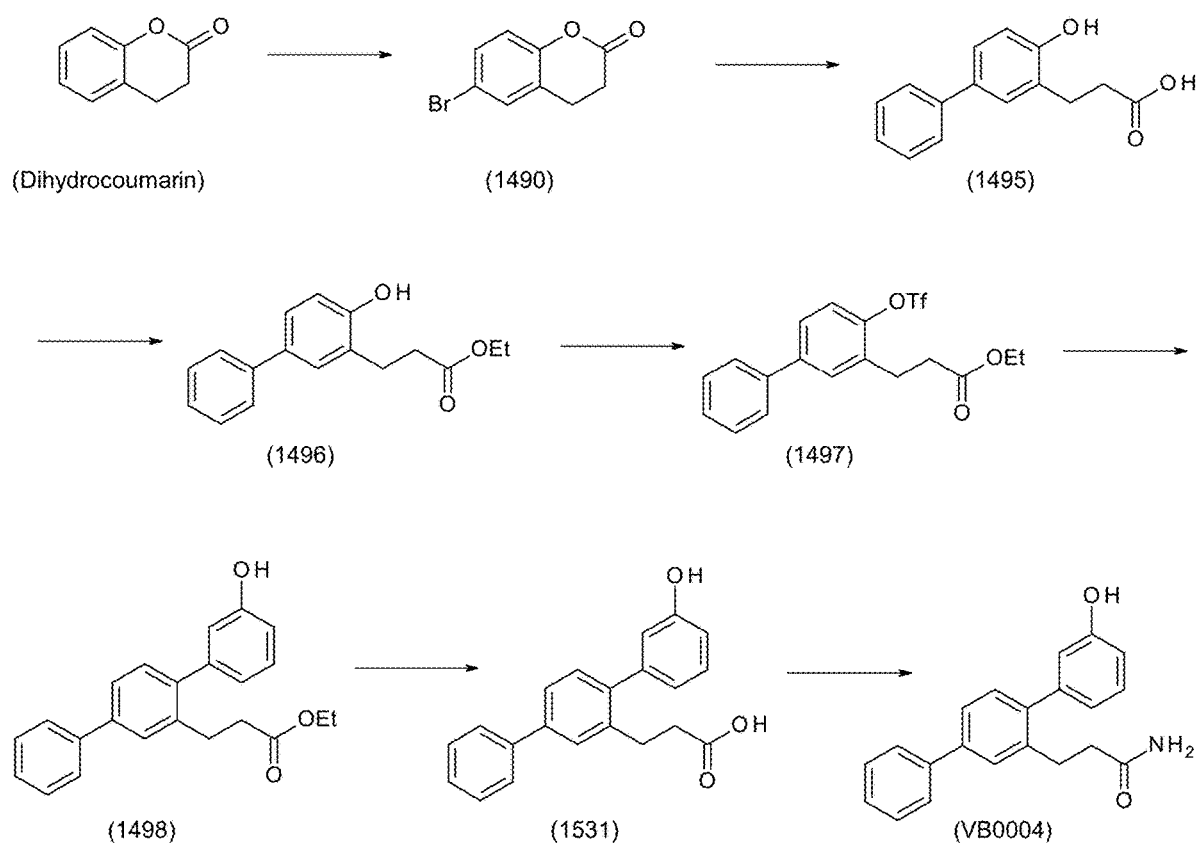
FIG. 1: Method for synthesizing VB0004.

The present invention relates to methods of synthesizing VB0004 and intermediates thereof.

As used herein, "VB004" refers to the compound of Formula I, "dihydrocoumarin" refers to the compound of Formula II, "1490" refers to the compound of Formula III, "1495" refers to the compound of Formula IV, "1496" refers to the compound of Formula V, "1497" refers to the compound of Formula VI, "1498" refers to the compound of Formula VII, and "1531" refers to the compound of Formula VIII.

As used herein, the abbreviations Me, Et, Ph, Ms, Ac, Tf represent methyl, ethyl, phenyl, methanesulfonyl, acetyl and trifluoromethanesulfonyl respectively. The abbreviations NMR, GC, TLC and UPLC represent Nuclear Magnetic Resonance, Gas Chromatography, Thin Layer Chromatography and Ultra High Performance Liquid Chromatography, respectively.

A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

Compounds of the present invention may exist in particular geometric or stereoisomeric forms. The present invention contemplates all such compounds, including cis- and trans-isomers, (R)- and (S)-enantiomers, diastereomers, (d)-isomers, (l)-isomers, the racemic mixtures thereof, and other mixtures thereof, as falling within the scope of the invention. All such isomers, as well as mixtures thereof, are intended to be included in this invention.

If, for instance, a particular enantiomer of a compound of the present invention is desired, it may be prepared by asymmetric synthesis, or by derivatization with a chiral auxiliary, where the resulting diastereomeric mixture is separated and the auxiliary group cleaved to provide the pure desired enantiomers. Alternatively, diastereomeric salts may be formed with an appropriate optically active acid or base, followed by resolution of the diastereomers thus formed by fractional crystallization or chromatographic means well known in the art, and subsequent recovery of the pure enantiomers.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

The present invention also contemplates pharmaceutically acceptable salts of the compounds. The term "pharmaceutically acceptable salt" includes both acid and base addition salts and refers to salts which retain the biological effectiveness and properties of the free bases or acids, and which are not biologically or otherwise undesirable. The pharmaceutically acceptable salts are formed with inorganic or organic acids or bases, and can be prepared in situ during the final isolation and purification of the compounds, or by separately reacting a purified compound in its free base or acid form with a suitable organic or inorganic acid or base, and isolating the salt thus formed.

The present invention also contemplates pharmaceutical compositions which include the compounds of the present invention, in conjunction with acceptable pharmaceutical excipients. The term "pharmaceutically acceptable excipient" as used in the context of the present invention means any pharmaceutically acceptable inactive component of the composition. As is well known in the art excipients include diluents, buffers, binders, lubricants, disintegrants, colorants, antioxidants/preservatives, pH-adjusters, etc. The excipients are selected based on the desired physical aspects of the final form: e.g. obtaining a tablet with desired hardness and friability being rapidly dispersible and easily swallowed etc. The desired release rate of the active substance from the composition after its ingestion also plays a role in the choice of excipients. Pharmaceutical compositions may include any type of dosage form such as tablets, capsules, powders, liquid formulations, delayed or sustained release, patches, snuffs, nasal sprays and the like. The physical form and content of the pharmaceutical compositions contemplated are conventional preparations that can be formulated by those skilled in the pharmaceutical formulation field and are based on well established principles and compositions described in, for example, Remington: The Science and Practice of Pharmacy, 19th Edition, 1995; British Pharmacopoeia 2000 and similar formulation texts and manuals.

For example, where the compounds or compositions are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent.

The present invention will now be described in more detail with reference to specific but non-limiting examples describing specific compounds and methods of use. It is to be understood, however, that the detailed description of the specific compounds and methods is included solely for the purpose of exemplifying the present invention. It should not be considered in any way as a restriction on the broad description of the inventive concept as set out herein.

EXAMPLES

Example 1—Synthesis Method

Synthesis Summary

The method of synthesizing VB0004 is modified as shown in FIG. 1. Surprisingly, it was found that the ring-opened acid, 3-(2-hydroxy-5-phenyl-phenyl)propanoic acid (1495) was able to be produced directly from the Suzuki reaction of 6-bromochroman-2-one (1490) as shown in FIG. 1. Briefly, 1495 was synthesized in two steps from dihydrocoumarin. 1495 was converted to ethyl 3-(2-hydroxy-5-phenyl-phenyl)propanoate (1496) by a Fischer esterfication of a carboxylic acid. The preparation of ethyl 3-[5-phenyl-2-(trifluoromethylsulfonyloxy) phenyl]propanoate (1497) involved the transformation of the 1496 phenol into the corresponding triflate. The triflate is a functional group that is suitable for Suzuki coupling and the production of ethyl 3-[2-(3-hydroxyphenyl)-5-phenyl-phenyl]propanoate (1498). A basic hydrolysis reaction of 1498 was then used to produce 3-[2-(3-hydroxyphenyl)-5-phenyl-phenyl]propanoic acid (1531). The final reaction step to convert 1531 into the corresponding amide involved bubbling ammonia gas through a solution of the activated carboxylic acid, followed by isolation of the VB0004 product by precipitation.

Synthesis of 1490

1490 was synthesized from dihydrocoumarin.

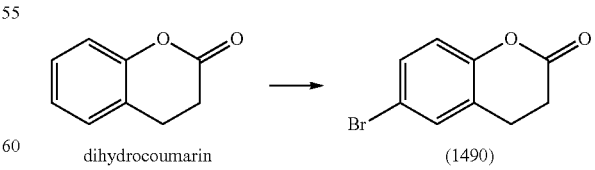

A solution of bromine (155 ml) in dichloromethane (500 ml) was added during 30 min to a solution of 3,4-dihydro-coumarin (450 g, 0.3 mol) in dichloromethane (2000 ml). The mixture was stirred overnight at 15° C., then diluted with dichloromethane (2000 ml), and washed with aqueous sodium bicarbonate (2×1000 ml) followed by water (1000 ml). The solution was dried over magnesium sulphate, filtered, and concentrated under reduced pressure. The residue was washed with petroleum ether (2×500 ml), and filtrate concentrated. The solid was recrystallised from dichloromethane/petroleum ether to give the bromide (BM1490) as thick white crystals (471 g, 74%).

Synthesis of 1495

1495 was produced from 1490 by a Suzuki reaction.

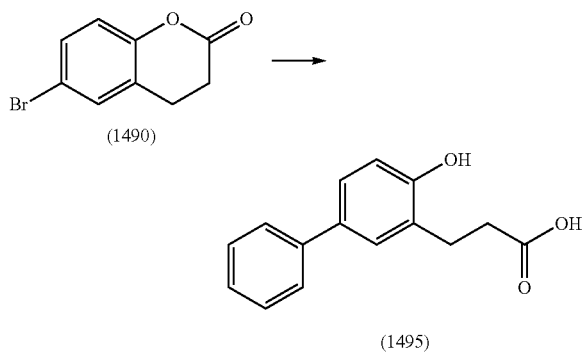

Figure 2:
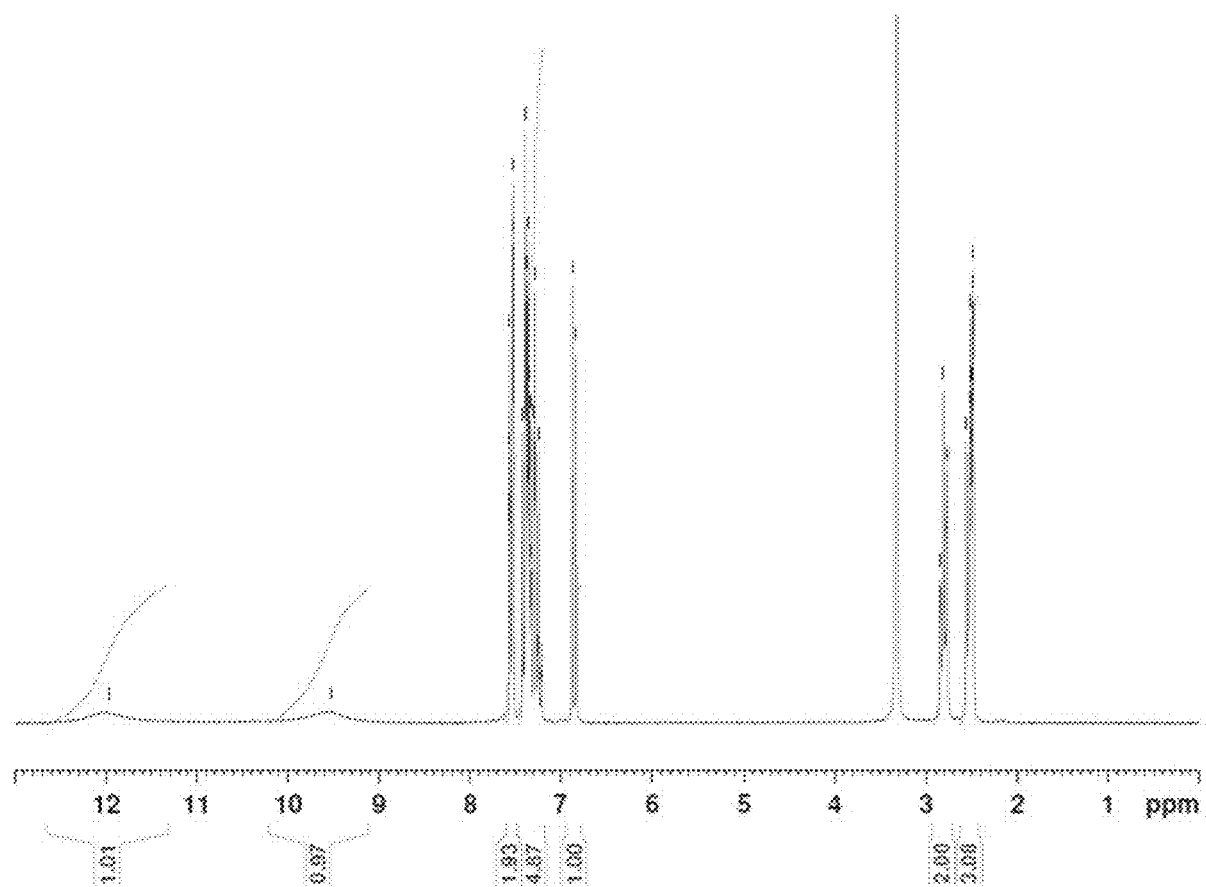
FIG. 2: 1H NMR spectrum for 3-(2-hydroxy-5-phenyl-phenyl)propanoic acid (1495).
Figure 3:
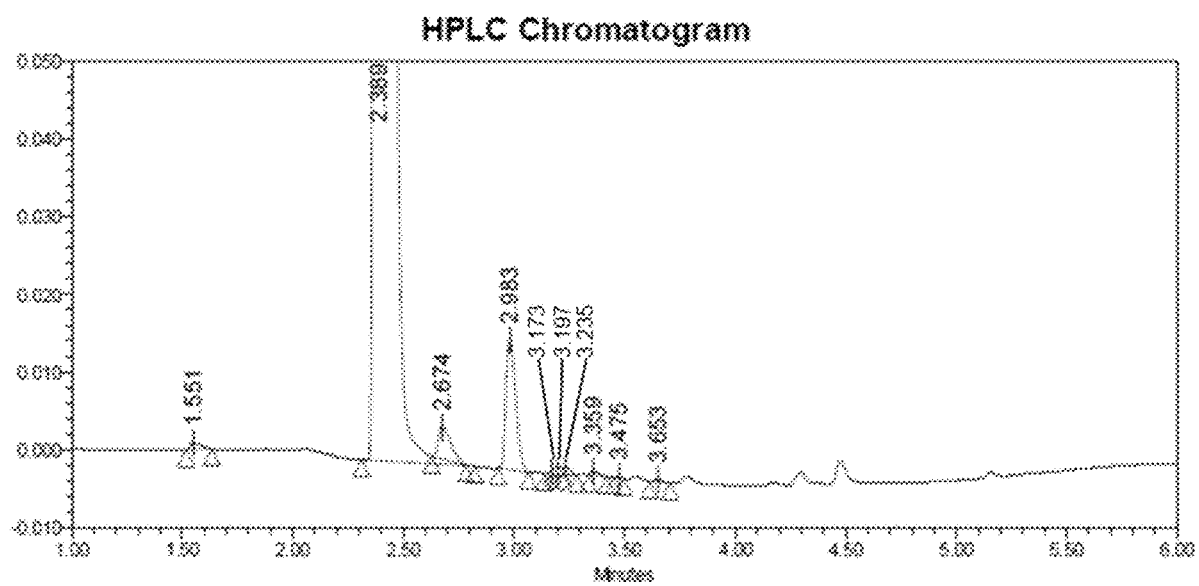
FIG. 3: UPLC results for 1495.

BM1490 (140 g, 0.617 mol) was dissolved in a solution of KOH (69 g, 1.23 mol) in water (500 mL) at 70° C. A solution of phenyl boronic acid (75.18 g, 0.617 mol) in KOH (69 g, 1.23 mol) and water (500 mL) was added and the temperature reduced to 60° C. and allowed to equilibrate. Palladium acetate (1.4 g) was added and the reaction stirred at 60° C. overnight. The reaction mixture was cooled to room temperature and diluted with water (300 mL). The aqueous solution was then washed with toluene (2×500 ml) and petrol (500 mL). Ice was added and concentrated hydrochloric acid was added dropwise until fully acidified. The solid was filtered. The solid was then dissolved in EtOAc (1.2 L) and activated carbon added. The mixture was stirred at ambient temperature for 1 hour. The mixture was filtered, washed with water (300 mL) and brine (200 mL), dried over magnesium sulphate and concentrated to give an off-white solid (110 g, 74%) with GC purity >98%. Analysis of the 1495 product by $^1$H NMR and UPLC shows that it has a purity >99% and analysis by ICP-MS indicated a residual palladium content of 3 ppm (FIGS. 2 and 3).

Synthesis of 1496

The reaction to produce 1496 is a Fischer esterification of a carboxylic acid. The reaction proceeds in quantitative yield without requiring purification of the 1496 product.

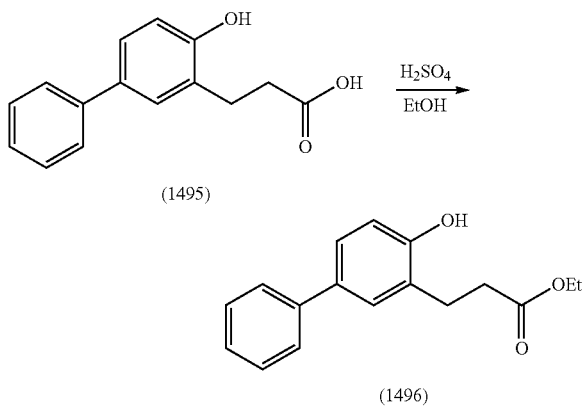

Figure 4:
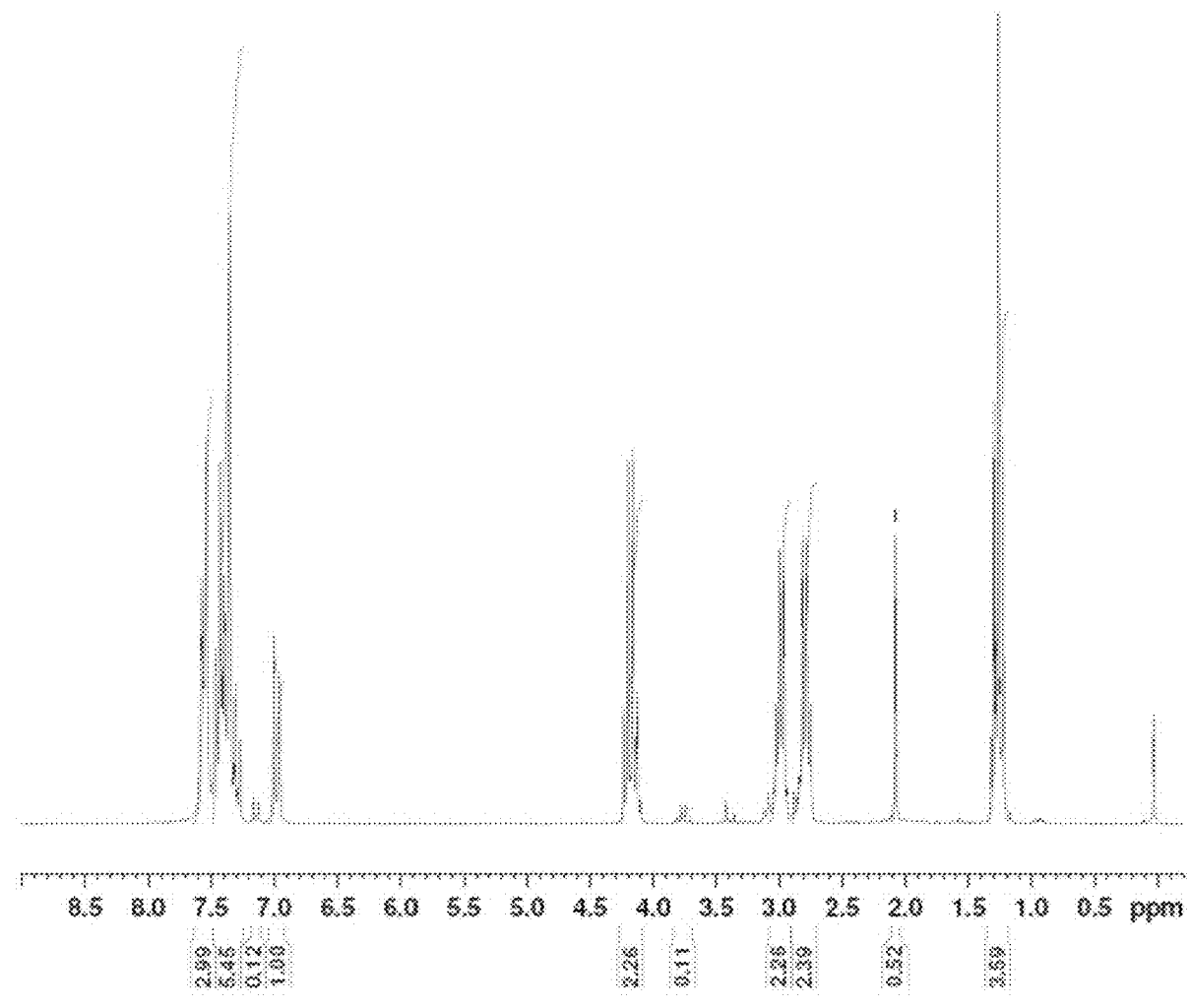
FIG. 4: 1H NMR spectrum for ethyl 3-(2-hydroxy-5-phenyl-phenyl)propanoate (1496).

1495 (136.5 g, 563 mmol) was dissolved in ethanol (900 mL) and concentrated sulphuric acid (2.2 mL) was added. The reaction mixture was refluxed overnight. After this time, TLC analysis (silica gel plates, 7:3 petrol/ethyl acetate, UV detection) showed the reaction to be complete. The reaction mixture was cooled to ambient temperature and solid NaHCO$_3$ (100 g) was added. The resulting slurry was stirred for 30 minutes. The mixture was filtered, washed with ethanol and concentrated. The crude product was dissolved in ethyl acetate (1 L) and washed with saturated aqueous NaHCO$_3$ solution (600 mL), followed by 1M aqueous HCl solution (600 mL). The organic phase was dried over MgSO$_4$ (40 g), filtered, washed with ethyl acetate and concentrated to afford a clear, viscous orange-brown liquid (152.7 g, quantitative yield). This material was used in the subsequent step without further purification. The $^1$H NMR spectrum for 1496 is shown in FIG. 4.

Synthesis of 1497

This step involves the transformation of the phenol of 1496 into the corresponding triflate, which is a functional group that is suitable for the Suzuki coupling in the next step. 1497 was used without further purification. However, 1497 can be recrystallised from methanol to form a low melting solid. 1497 was stored at −20° C. without noticeable degradation over a period of 5 months.

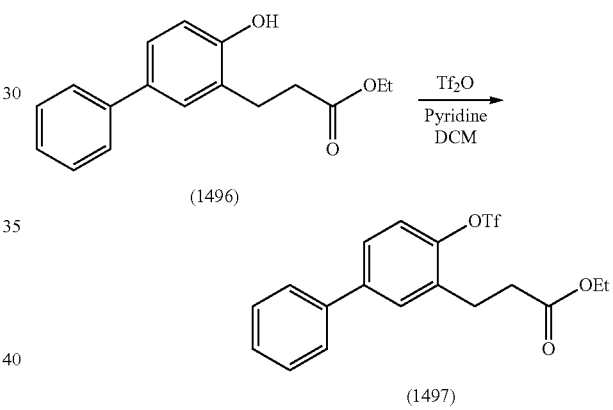

Figure 5:
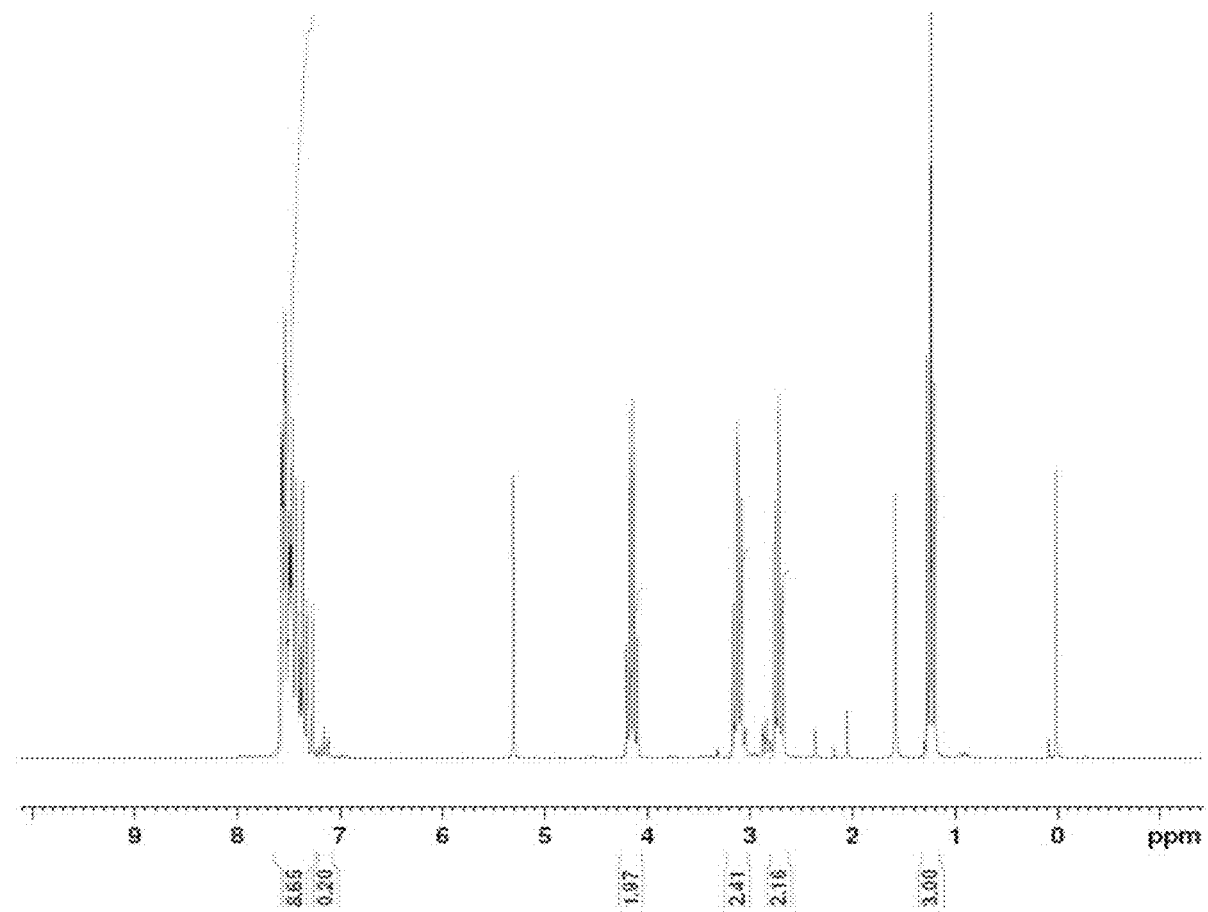
FIG. 5: 1H NMR spectrum for ethyl 3-[5-phenyl-2-(trifluoromethylsulfonyloxy) phenyl] propanoate (1497).

A stirred solution of 1496 (150 g, 553 mmol) in dichloromethane (1.2 L) and pyridine (134 mL, 1.66 mol) was cooled to 0° C. Triflic anhydride (107 mL, 636 mmol) was added dropwise over 20 minutes at 0° C. and the resultant mixture was left to warm to ambient temperature and was stirred at ambient temperature overnight. After this time, TLC analysis (silica gel plates, 7:3 petrol/EtOAc, UV detection) showed the reaction to be complete. The solution was diluted with dichloromethane (500 mL) and washed with aqueous 1 M HCl (2×600 mL). The aqueous portions were then extracted with dichloromethane (200 mL) and the combined organic extracts washed with water (2×500 mL). The resulting solution was charged with MgSO$_4$ (30 g) and activated carbon (8 g) and stirred for 1 hour. The suspension was filtered, washed with dichloromethane and concentrated to afford an orange oil (215 g, 97%). Intermediate 1497 was used without further purification. The $^1$H NMR spectrum for 1497 is shown in FIG. 5.

Synthesis of 1498 and 1531

The reaction to produce 1498 is a Suzuki coupling reaction which brings together the two main components which form VB0004. A subsequent basic hydrolysis reaction of 1498 affords the corresponding acid as an easily-handled solid.

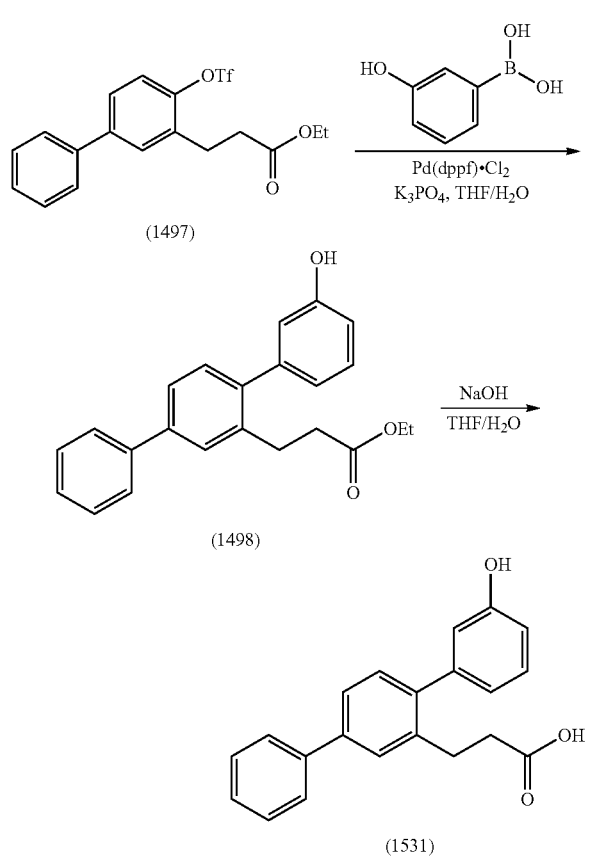

(1497)

(1498)

(1531)

The manufacture of 1498 on a large scale used four equivalents of the K$_3$PO$_4$ base. It was later determined that the number of equivalents of base could be reduced to 1.5 equivalents, which facilitated the work-up as there were no longer significant quantities of inorganic solids in the reaction mixture. A filtration step was originally required to filter off the insoluble solids. This filtration step helped to reduce the emulsions that had formed and enabled the separation of the organic and aqueous phases. The reduction in the number of equivalents of base to 1.5 equivalents resulted in a much improved work-up and significantly reduced the formation of emulsions. The filtration step can potentially be removed from the work-up below as there did not appear to be any insoluble solids remaining in the bi-phasic mixture during aqueous work-up. Considerable work was undertaken to optimise the recrystallisation solvent for the purification of 1531. To a stirred solution of 1497 (10.31 g, 25.6 mmol) and 3-hydroxyphenylboronic acid (3.71 g, 26.9 mmol) in tetrahydrofuran (100 mL) was added a suspension of K$_3$PO$_4$ (8.15 g, 38.4 mmol) in water (10 mL). The reaction mixture was heated to 80° C. before addition of the palladium catalyst ([1,1'-Bis(diphenylphosphino)ferrocene]Dichloropalladium(II) complex with dichloromethane, Pd(dppf).Cl$_2$.CH$_2$Cl$_2$, 1.0 g). No appreciable increase in temperature was observed on addition of the catalyst. The black solution was then stirred at 80° C. overnight after which time TLC analysis (silica gel plates, 4:1, petrol/EtOAc, UV detection) showed that the reaction was complete.

The reaction mixture was concentrated to remove tetrahydrofuran. Water (100 mL) and ethyl acetate (100 mL) were added and the mixture was acidified with concentrated aqueous HCl (20 mL). The phases were separated and the aqueous phase was extracted with ethyl acetate (100 mL). The combined organic extracts were filtered through glass fibre paper (which may, for example, be replaced with Celite if required) and then washed with brine (500 mL). The organic extract was charged with MgSO$_4$ (10 g) and activated carbon (3 g), and the resulting suspension was stirred for 45 minutes. The mixture was filtered, washed with ethyl acetate and concentrated to afford a viscous dark brown oil.

Figure 6:
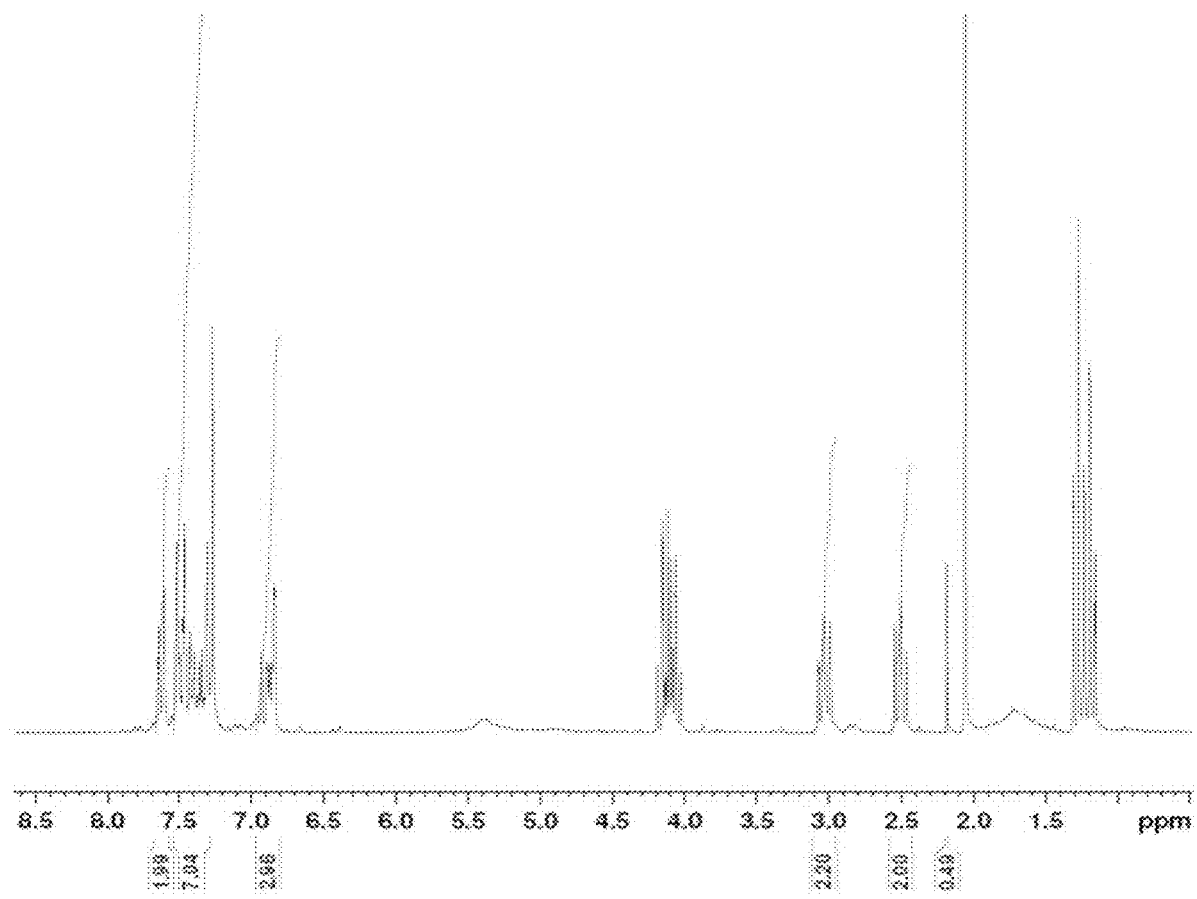
FIG. 6: 1H NMR spectrum for ethyl 3-[2-(3-hydroxyphenyl)-5-phenyl-phenyl] propanoate (1498).
Figure 7:
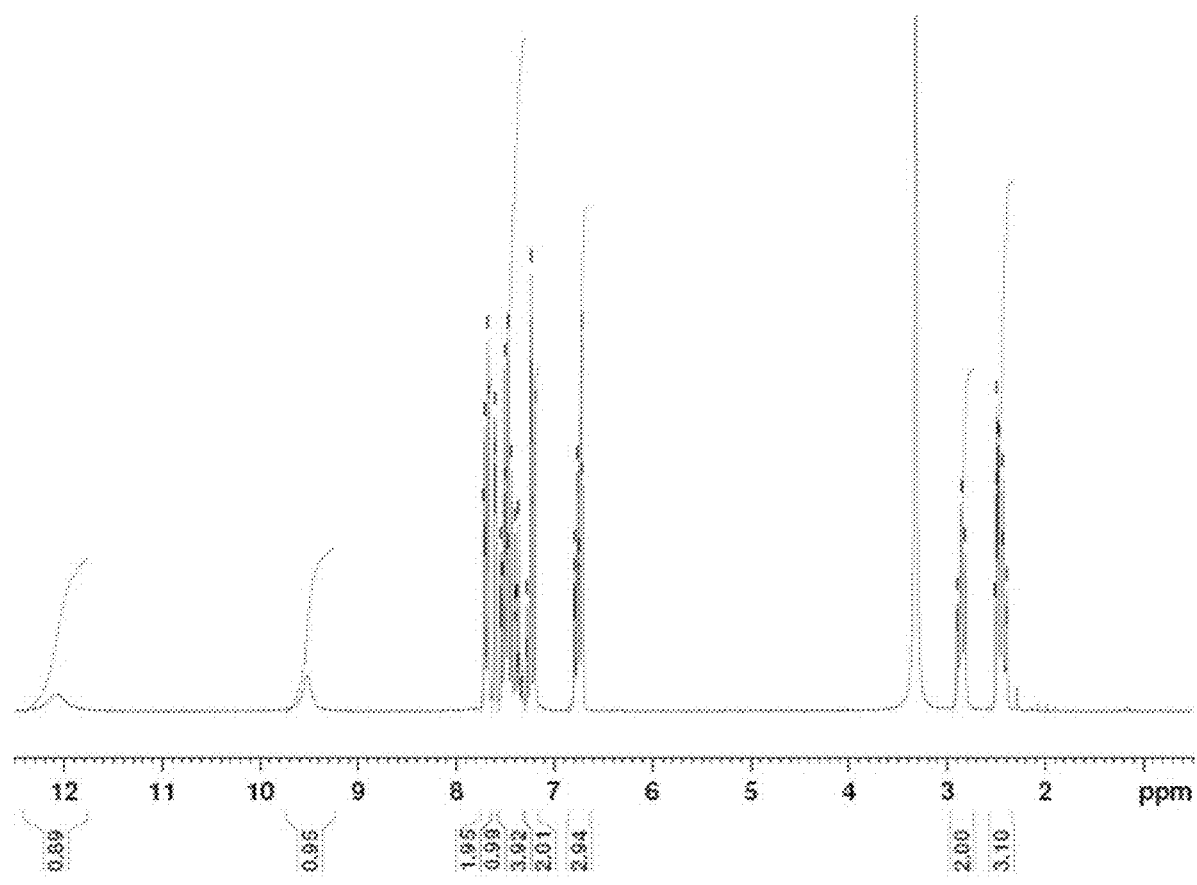
FIG. 7: NMR spectrum for produce 3-[2-(3-hydroxyphenyl)-5-phenyl-phenyl] propanoic acid (1531).
Figure 8:
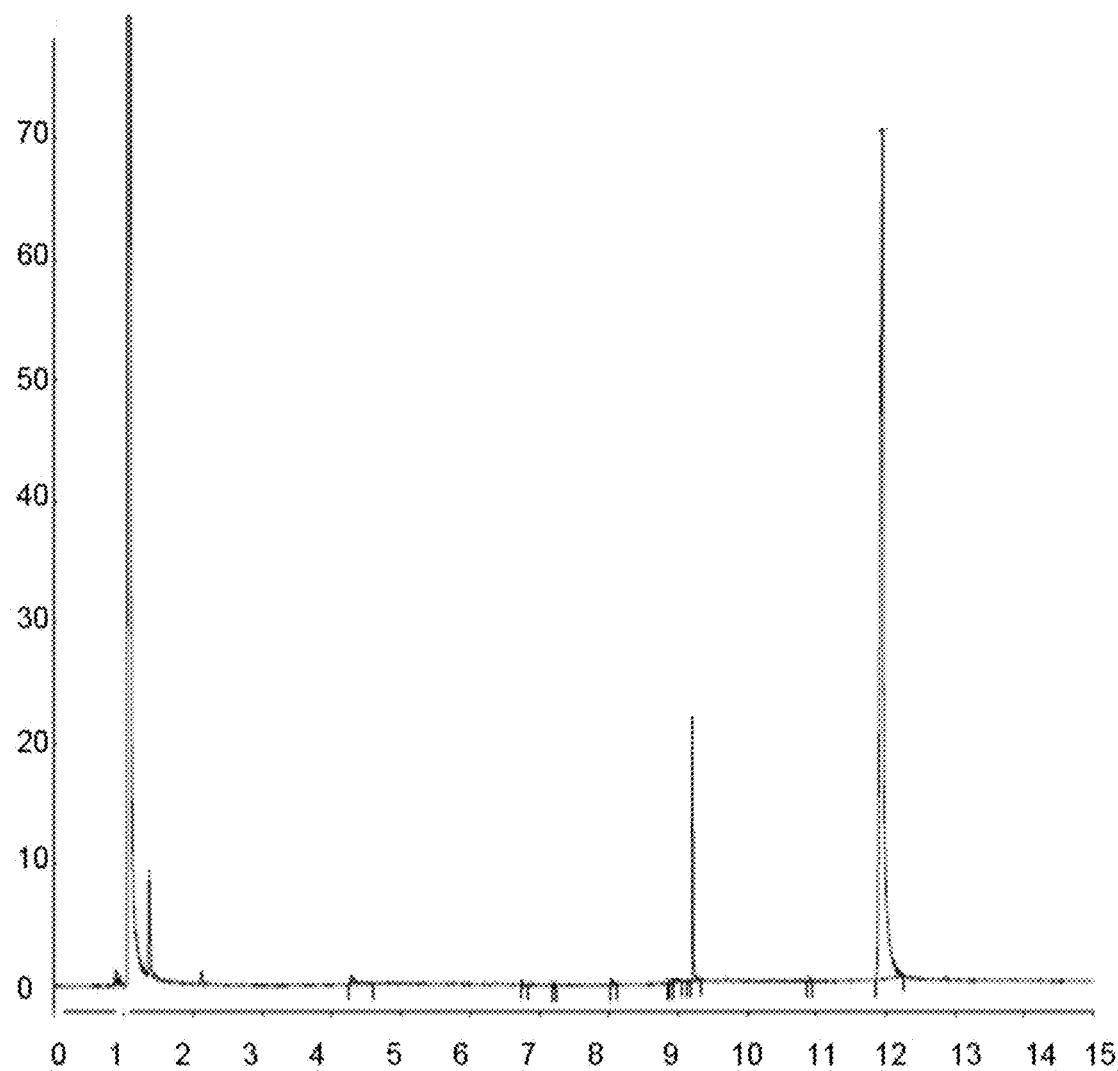
FIG. 8: GC results for 1498.
Figure 9:
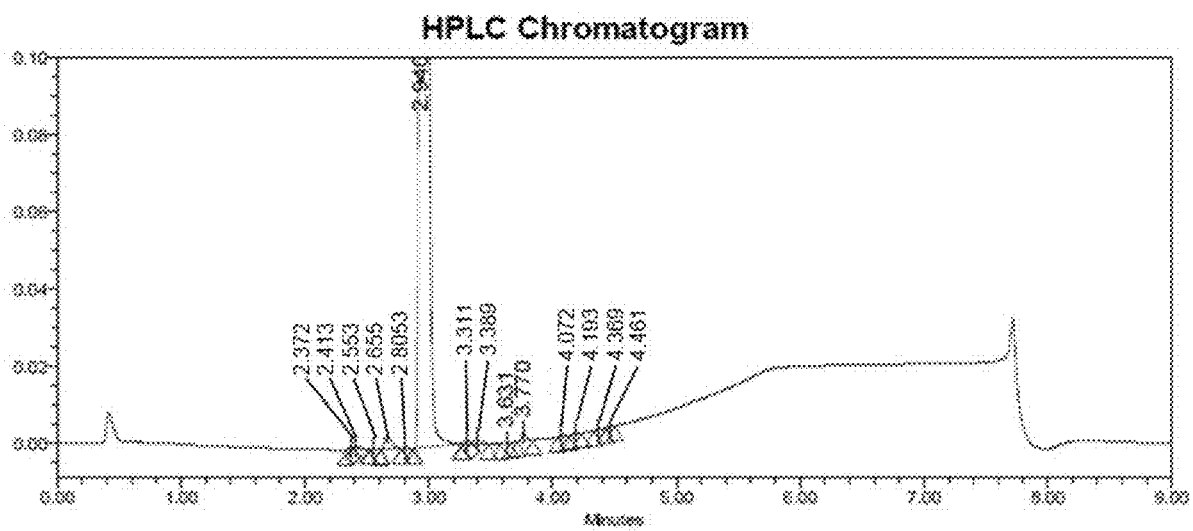
FIG. 9: UPLC results for 1531.

To a stirred solution of 1498 (103 g, 297 mmol) in tetrahydrofuran (250 mL) was added a solution of NaOH (35.7 g, 892 mmol) in water (600 mL). The resulting solution was heated to 60° C. for 2 hours, after which time TLC (silica gel plates, 1:1 petrol:EtOAc, UV detection) showed the reaction to be complete. The tetrahydrofuran was removed by concentration and the reaction mixture was diluted with water (400 mL). The aqueous phase was washed with toluene (3×500 ml) and with petrol (400 mL). The aqueous extract was treated with HCl to make the mixture acidic. The solid which formed was filtered, washed with water and dried to give the crude product. The crude solid was recrystallised from toluene (400 mL) to afford 1531 as a pale brown solid (40.9 g, 53%). This purification step removes many of the impurities that were carried through from earlier steps in the process. $^1$H NMR spectrum for 1498 and 1531 are shown in FIGS. 6 and 7, the GC results for 1498 are shown in FIG. 8 and the UPLC results for 1531 are shown in FIG. 9.

Preparation of VB0004

The final reaction step to convert the acid into the corresponding amide proved to be challenging. Problems included the formation of ester by-products and difficulties with purification of the final product. The present method preferably involves bubbling ammonia gas through a solution of the activated carboxylic acid, followed by isolation of the product by precipitation. The gas was bubbled through the solution in 30 minute portions, followed by several hours of heating between the two additions of ammonia gas. The subsequent methanol-aqueous ammonia step was necessary to achieve complete conversion to the amide.

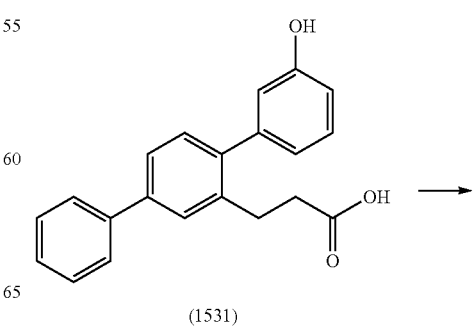

(1531)

-continued

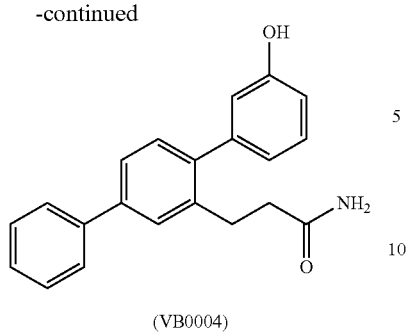

(VB0004)

Figure 10:
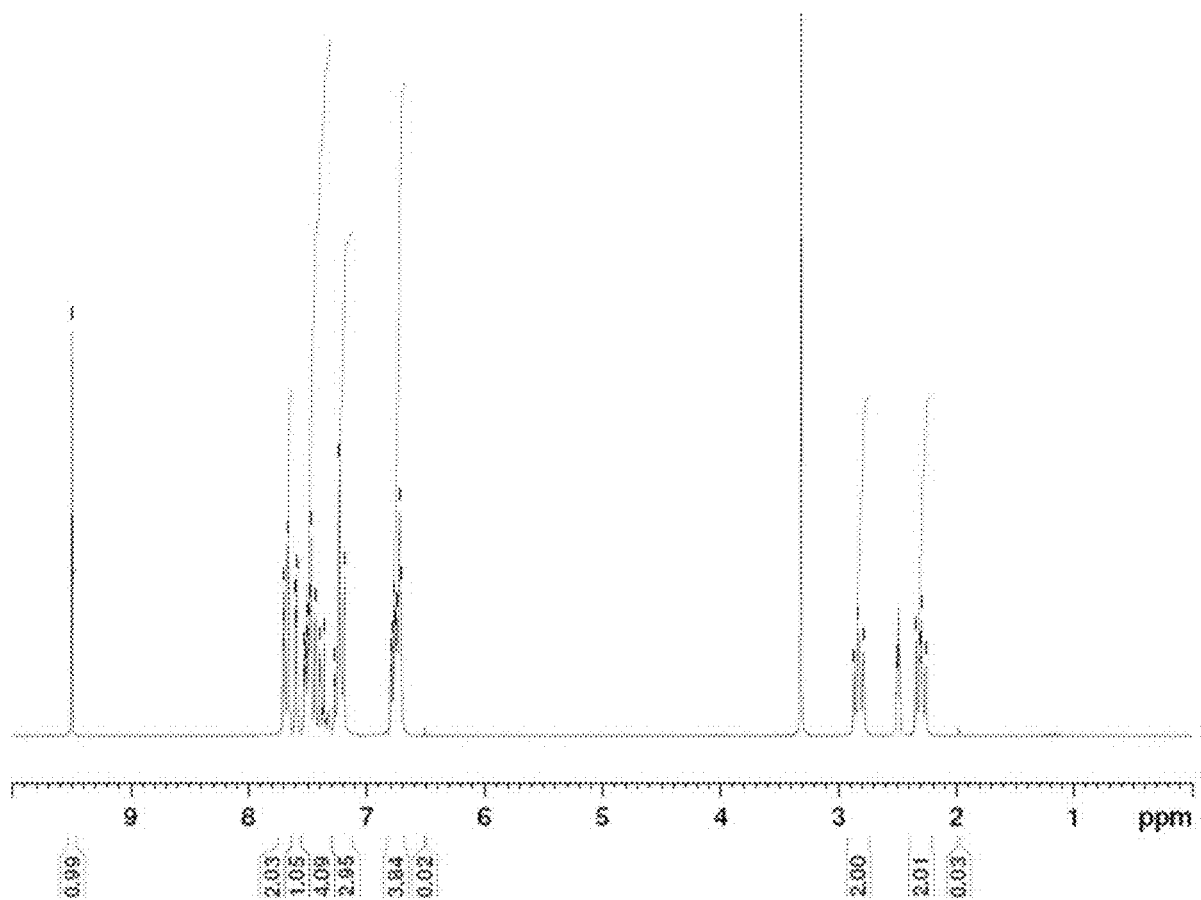
FIG. 10: 1H NMR spectrum for VB0004.
Figure 11:
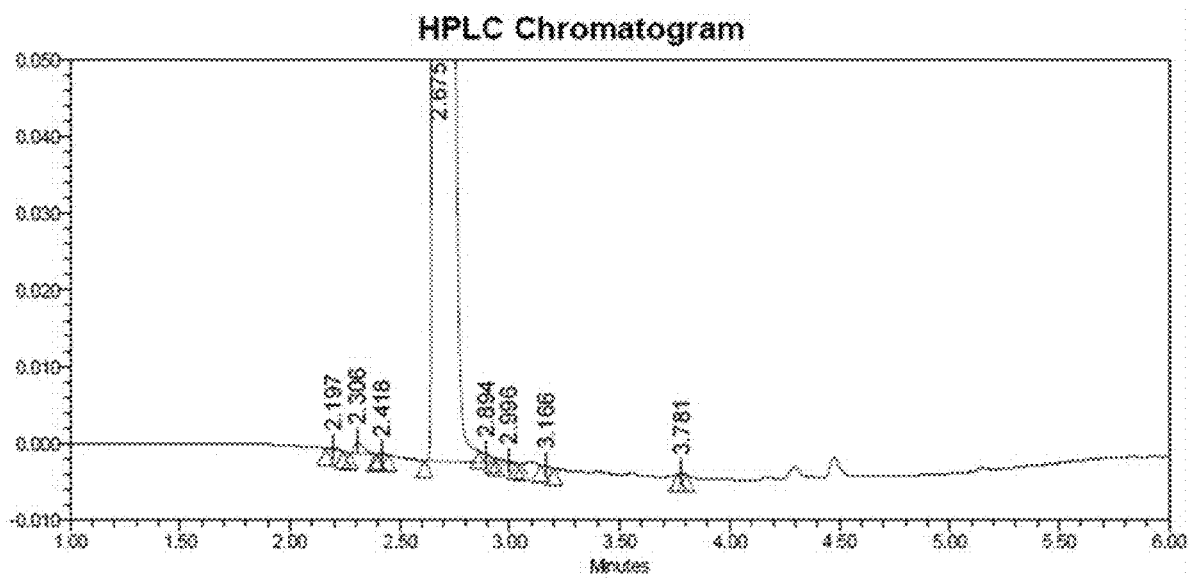
FIG. 11: UPLC results for VB0004.
Figure 12:
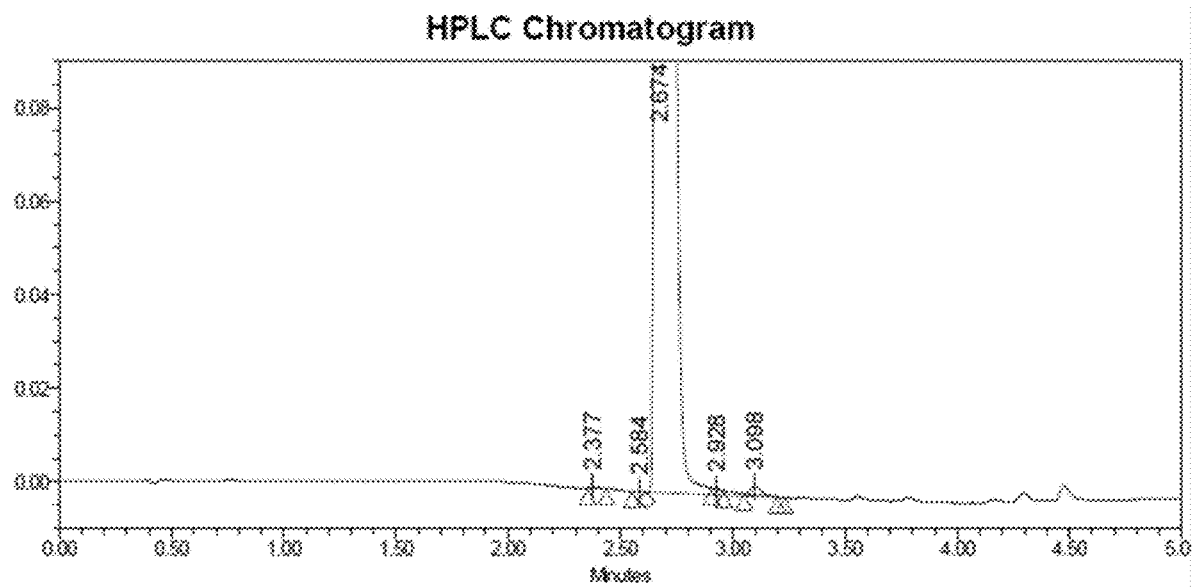
FIG. 12: UPLC results for VB0004 reference.

To a solution of 1531 (25 g, 79.0 mmol) in tetrahydrofuran (250 mL) was added 1,1-carbonyldiimidazole (17.5 g, 107.9 mmol) portion-wise over 10 minutes. The reaction mixture was heated to reflux and stirred under nitrogen for 18 hours. After this time, the reaction mixture was cooled to 5° C. (ice bath) and ammonia gas was bubbled into the mixture for 30 minutes. The reaction mixture was heated to reflux for 3 hours before repeating the ammonia gas bubbling into the mixture at 5° C. for 30 minutes. The reaction mixture was then heated to reflux overnight. After this time, tetrahydrofuran was removed by concentration under reduced pressure and a mixture of MeOH (50 mL) and 25% aqueous ammonia solution (50 mL) was added. The reaction mixture was heated to 70° C. for 2 hours. The solution was cooled to ambient temperature and was concentrated to dryness. The residue was slurried in aqueous 1M HCl solution (120 mL) and filtered. The solid was dissolved in ethyl acetate (100 ml), treated with $MgSO_4$ (5 g) and activated carbon (1 g), filtered and concentrated to give an off-white white solid. The solid was purified by dissolution in ethyl acetate, followed by the addition of toluene as an anti-solvent to precipitate out the product. The solid was filtered, washed with toluene and dried in a vacuum oven at 50° C. to give the VB0004 product as a white solid (17.0 g, 68%). The 1H NMR spectrum for VB0004 is shown in FIG. 10. Analysis of the product by UPLC indicated that it had a purity of 99.91% (FIG. 11), which compared well with the VB0004 reference material that had a purity of 99.91% (FIG. 12). ICP-MS analysis showed that VB004 contained 1 ppm of residual palladium.

Example 2—Alternative Synthesis Methods

Figure 13:
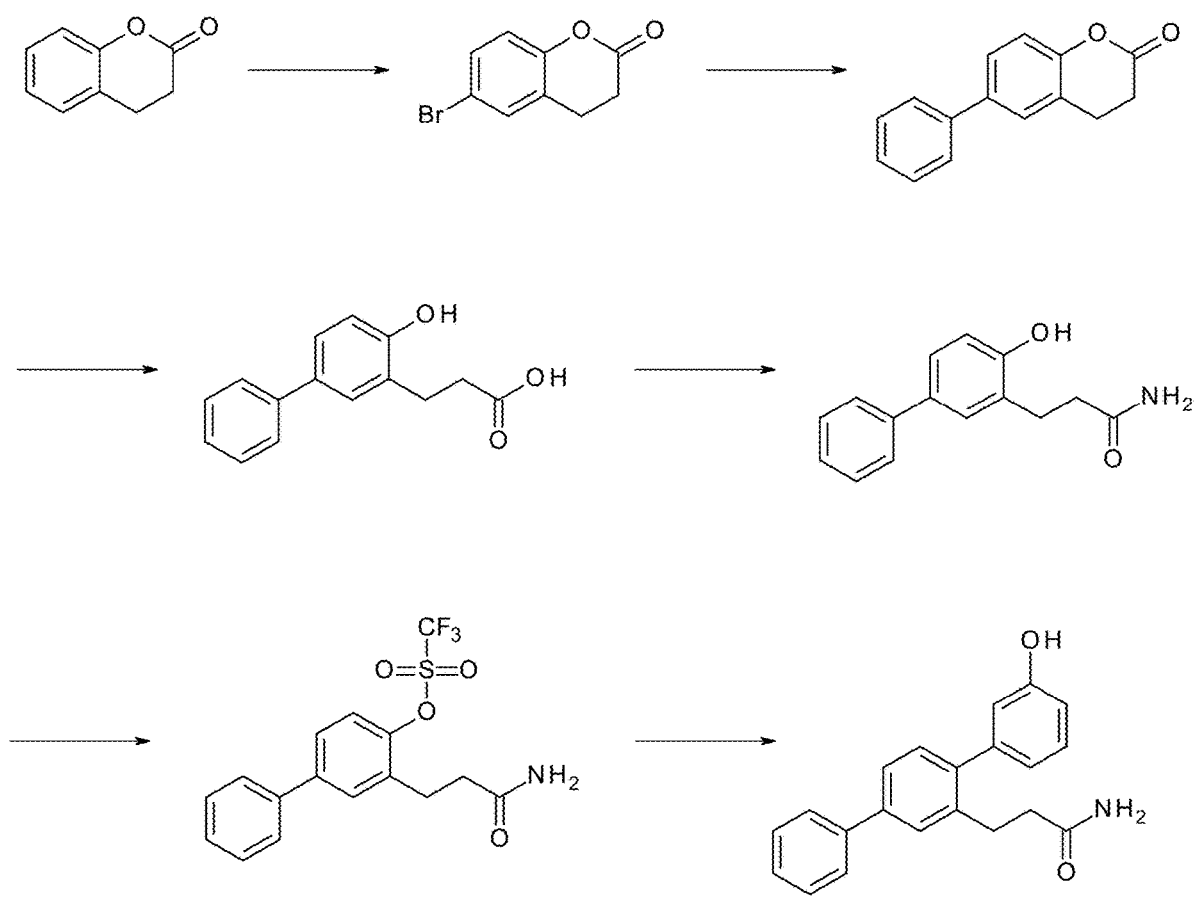
FIG. 13: Alternative method for synthesizing VB0004.
Figure 14:
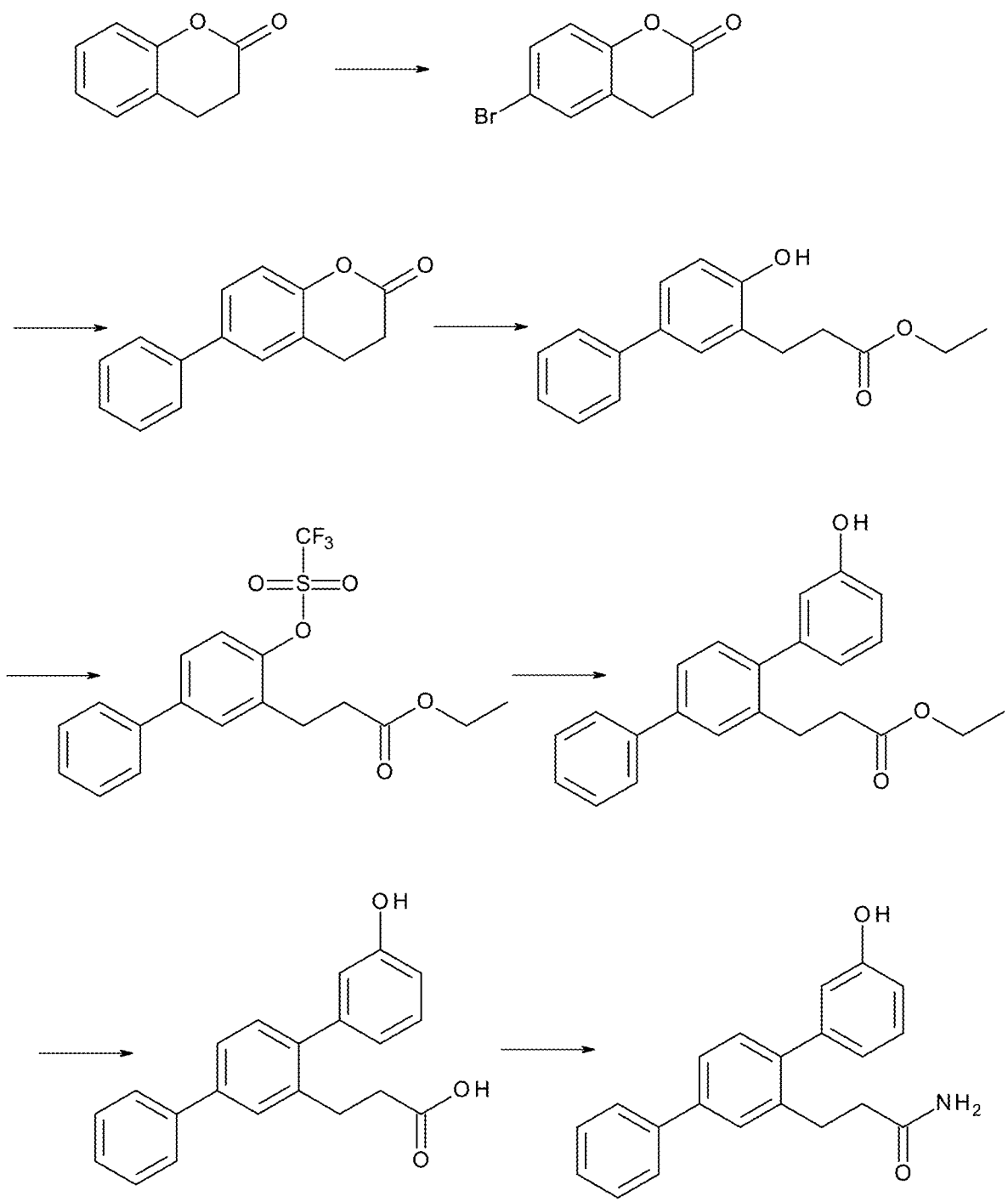
FIG. 14: Alternative method for synthesising VB0004.

VB0004 is also synthesisable from dihydrocoumarin by the methods shown in FIGS. 13 and 14.

The invention claimed is:

1. A compound selected from the group consisting of

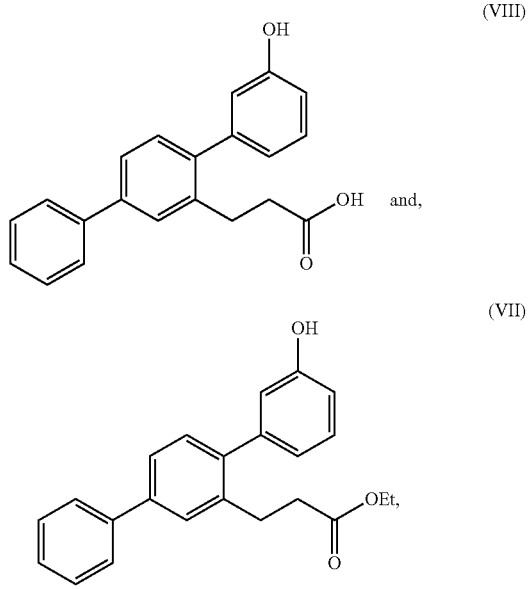

or a pharmaceutically acceptable salt thereof.

2. A method of producing a compound of Formula (I)

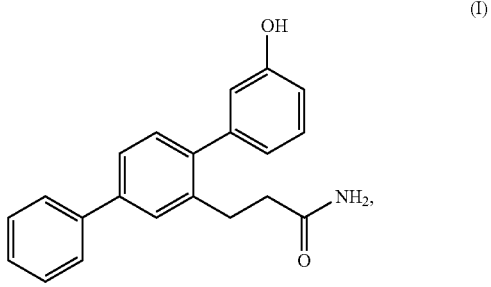 [SMILES: NC(=O)CCc1cc(-c2ccccc2)ccc1-c1cccc(O)c1]

or a pharmaceutically acceptable salt thereof comprising use of one or more compounds of claim 1.

* * * * *

UNITED STATES PATENT AND TRADEMARK OFFICE
CERTIFICATE OF CORRECTION

| | | |
|---|---|---|
| PATENT NO. | : 11,401,235 B2 | Page 1 of 1 |
| APPLICATION NO. | : 16/918439 | |
| DATED | : August 2, 2022 | |
| INVENTOR(S) | : Anthony Kaye et al. | |

It is certified that error appears in the above-identified patent and that said Letters Patent is hereby corrected as shown below:

On the Title Page

The Related U.S. Application Data Section Should read:
Division of application No. 15/761,862, filed as application No. PCT/AU2016/050875 on Sep. 21, 2016, now Pat. No. 10,752,578.

Signed and Sealed this
Third Day of January, 2023

Katherine Kelly Vidal
*Director of the United States Patent and Trademark Office*